United States Patent
Ginja et al.

(10) Patent No.: US 7,967,350 B2
(45) Date of Patent: Jun. 28, 2011

(54) SHOCK ABSORPTION MODULE FOR AN AUTOMOBILE

(75) Inventors: Stephane Ginja, Amberieu en Bugey (FR); Sebastien Charnaux, Journans (FR); Philippe Gilotte, Benonces (FR)

(73) Assignee: Compagnie Plastic Omnium, Lyons (FR)

( * ) Notice: Subject to any disclaimer, the term of this patent is extended or adjusted under 35 U.S.C. 154(b) by 0 days.

(21) Appl. No.: 12/449,034

(22) PCT Filed: Jan. 22, 2008

(86) PCT No.: PCT/FR2008/050099
§ 371 (c)(1),
(2), (4) Date: Jan. 26, 2010

(87) PCT Pub. No.: WO2008/110709
PCT Pub. Date: Sep. 18, 2008

(65) Prior Publication Data
US 2010/0127520 A1   May 27, 2010

(30) Foreign Application Priority Data
Jan. 23, 2007   (FR) ..................... 07 52842

(51) Int. Cl.
*B60R 19/30* (2006.01)

(52) U.S. Cl. .............. 293/136; 296/187.03; 296/187.09; 188/371

(58) Field of Classification Search ............ 293/121, 293/115, 109, 135, 136; 296/187.03, 187.04, 296/187.09; 188/371, 376, 377
See application file for complete search history.

(56) References Cited

U.S. PATENT DOCUMENTS

| 3,692,345 | A * | 9/1972 | Dumontier | 293/120 |
| 6,467,822 | B1 | 10/2002 | Leng | |
| 6,648,383 | B2 * | 11/2003 | Vismara et al. | 293/120 |
| 7,399,015 | B2 * | 7/2008 | Patel et al. | 293/133 |
| 2002/0101085 | A1 | 8/2002 | Gehringhoff et al. | |

FOREIGN PATENT DOCUMENTS

| DE | 613 939 C | 5/1935 |
| EP | 1 036 715 A2 | 9/2000 |
| EP | 1 067 039 A1 | 1/2001 |
| EP | 1 352 810 A2 | 10/2003 |
| EP | 1 698 520 A1 | 9/2006 |
| FR | 2 821 817 A3 | 9/2002 |
| FR | 2 840 573 A1 | 12/2003 |

* cited by examiner

*Primary Examiner* — Lori L Lyjak
(74) *Attorney, Agent, or Firm* — Oliff & Berridge, PLC (57) ABSTRACT

The invention provides an impact absorber module for a motor vehicle, the module comprising: a top transverse element for bearing against an impact beam of the vehicle; a bottom transverse element and two uprights connecting the top and bottom transverse elements together so as to form substantially a frame referred to as an absorber frame, the bottom transverse element or one of the two uprights being designed to bear against a bottom structural part of the vehicle; and a wall forming an air guide and extending from the top transverse element towards a radiator of the vehicle.

17 Claims, 5 Drawing Sheets

SHOCK ABSORPTION MODULE FOR AN AUTOMOBILE

TECHNICAL FIELD

The present invention relates to the field of absorbing impacts in motor vehicles, in particular front impacts of the insurance impact type.

STATE OF THE ART

With respect to impacts, motor manufacturers comply with specifications setting out four main categories of impacts, namely:

high speed type impacts that correspond to a front or rear impact of the vehicle against a rigid or deformable obstacle. For a front impact, the vehicle speed is at least 56 kilometers per hour (km/h) and the objective is to protect the occupants of the vehicle;

insurance type impacts at about 15 km/h against a stationary wall, such as the Danner impact or the AZT impact, or at about 8 km/h against the corner of the wall or against a post (post impacts, IIHS standard), that are handled with the objective of limiting damage and the associated costs of repair;

small impacts, or parking type impacts, at a speed of less than 8 km/h, that are handled with the objective of not damaging the outside of the bumper skin; and regulation pedestrian impacts (leg, femur, and head).

An impact absorber system is described in U.S. Pat. No. 6,467,822 and serves in particular, in the event of an insurance impact, to prevent deformation of the side rails, in particular for the purpose of sparing the radiator and other members located behind it. That system comprises a top transverse element bearing against an impact beam and capable of absorbing energy by compressing against the impact beam. The impact beam itself bears against two front side rails of the vehicle. Energy is absorbed by compressing the transverse element.

Problem Posed By the State of the Art

In order to absorb sufficient energy in the event of an insurance impact, it is necessary for the transverse element to absorb the majority of the impact energy, and therefore for its depth in the longitudinal direction of the vehicle to be greater than some minimum value, thereby imposing a certain amount of vehicle overhang in the longitudinal direction, i.e. a certain length for front portion of the vehicle between its side rails and the bumper skin.

This increase in overhang puts restrictions on the outside shape of the vehicle.

Proposed Solution

The invention seeks to provide an impact absorber system that has particularly good performance, but without thereby increasing the overhang of the vehicle in the longitudinal direction.

To this end, the invention provides an impact absorber module for a motor vehicle, the module comprising:

a top transverse element for bearing against an impact beam of the vehicle;

a bottom transverse element and two uprights connecting the top and bottom transverse elements together so as to form substantially a frame referred to as an absorber frame, the bottom transverse element or at least one of the two uprights being designed to bear against a bottom structural part of the vehicle; and a wall forming an air guide and extending from the top transverse element towards a radiator of the vehicle.

Particular Advantages

Because of the absorber frame formed by the top and bottom elements and by the uprights, energy absorption is provided not only by the top transverse element in combination with the impact beams, which are located at the same height as the vehicle side rails, but also by elements that are arranged below the side rails, in particular as a result of the bottom transverse element or the upright being compressed against said bottom structural part of the vehicle. As a result, energy absorption by the compression of elements takes place via a plurality of bearing faces and the total compression area of the absorbers is greater than in the state of the art. The bearing faces thus comprise not only the ends of the side rails (such as a fastener plate of the impact beam), but also a bearing face made available by the bottom structural part. Since the total bearing area is greater, the thickness of the absorber elements in the longitudinal direction can be decreased while still being capable of absorbing sufficient energy in the event of an impact, in particular an insurance impact.

It should be observed that the bottom structural part is configured so that it does not deform irreversibly in the event of an insurance type impact, i.e. it remains intact after such an impact. This part is thus different from a bearing piece designed to withstand no more than a pedestrian impact. Thus, the bottom structural part remains intact when subjected to a force that may be as great as 30,000 newtons.

Furthermore, because of the absorber frame, compatibility between vehicles is improved by offering an absorption area that is greater than in a conventional absorber system. The rigid structures of vehicles thus do not run the risk of constituting intrusive parts that are particularly dangerous and destructive for the other vehicle. Thus, because of its extent in the vertical direction, the absorber frame offers a larger impact area at the front of the vehicle, such that in the event of a collision the probability of encountering the energy absorber system of the other vehicle is particularly high.

Furthermore, because of the air-guide forming wall extending from the top transverse element towards the radiator, a particularly advantageous function that can be provided by the absorber module consists in guiding air that enters openings formed in the bumper skin towards the vehicle radiator. Since the absorber module is no longer in front of the radiator, it can provide a junction between the bumper skin and the vehicle radiator for guiding air. The frame shape of the absorber frame associated with the air-guide forming wall extending from the top transverse element enables the absorber module to define an air-guidance compartment that is particularly advantageous since there is no need to fit special air-guidance parts to the vehicle and there is thus no need to handle the clearances associated with such parts. Thus, the inventors of the present invention have had the idea of combining in a single module two technical fields that are conventionally separate in the automotive industry, i.e. the field of absorbing energy and the air-flow field.

Thus, an absorber system is made available in the form of a preassembled module comprising an absorber frame and an air-guide forming wall, which module is suitable for fitting to the vehicle, thereby limiting the number of parts that need to be fitted during vehicle assembly. The module may incorporate numerous functions: the function of handling impacts, in particular pedestrian impacts (via the bottom and top transverse elements), parking type impacts, and insurance type impacts, the function of reinforcing various parts of the vehicle, and the function of supporting other functional members of the vehicle such as bundles, sensors, fasteners, a horn, etc.

PARTICULAR EMBODIMENTS

In an embodiment of the invention, the absorber module defines a compartment for guiding air towards the radiator, the compartment being defined in particular by the inside wall of each of the uprights, the top wall of the bottom transverse element, and said air-guide forming wall extending from the top transverse element, each of these walls preferably extending as far as the radiator.

Optionally, the absorber module also includes air-guide means designed to be arranged between the impact beam and the radiator, preferably integrally molded with the air-guide forming wall extending from the top transverse element. Such guide means may be made up of tongues that can be folded behind the impact beam. They thus enable the space between the radiator and the rear portion of the beam to be plugged, which space is generally due to the presence of crash-boxes on the portions of the beam that are situated in register with the side rails.

In even more advantageous manner, the compartment for guiding air is a leaktight compartment suitable for guiding incoming air towards the radiator in leaktight manner. Since the elements for guiding air are all incorporated in the absorber module, preferably being obtained by molding, it is possible to obtain a compartment that is arranged to minimize air leakage between the air inlet(s) in the bumper skin and the radiator (the compartment presenting less than 5% air leakage). This considerably improves the air-guidance effect. It is also possible to envisage minimizing the dimensions of the cooling system, in particular by reducing the height of the radiator, so that it can be placed at a height that is lower than that of the side rails, thereby making it possible, under favorable conditions, to position the radiator beneath the impact beam, and thus reduce the overhang of the vehicle in the longitudinal direction.

The invention may also include one or more of the following characteristics.

The bottom and top transverse elements, the uprights, and the air-guide forming wall are made of plastics material, preferably obtained by molding. It can be understood that this technique is most advantageous from the point of view of the costs of fabrication and assembly, with a single part being used to handle most of the energy absorption specifications, in particular for pedestrian and insurance impacts, and also for providing leaktight guidance for the air that is guided by the absorption module. Fabricating a single part that performs all of these functions presents the particular advantage of giving rise to very few fabrication tolerances.

The bottom transverse element includes a bottom spoiler, preferably obtained by molding. Thus, the absorber module is also used to perform a function of guiding the air that passes under the engine and gearbox unit to ensure the vehicle is aerodynamic.

Each upright is designed to bear against a structural part including a bearing face and extending downwards from the end of each of the side rails. Thus, the uprights participate in energy absorption by being compressed against said bearing face. Preferably, the structural part comprises a brace, e.g. in the form of a right-angled triangle, that transfers the forces to which one of the uprights are subjected during compression to a bottom or side face of the side rail, or to an additional part associated with the side rails. This brace serves to reinforce the bearing part, enabling it to better withstand folding or other deformation in the event of an insurance type impact.

The structural part comprises bottom side rails, also referred to as motor vehicle cradle extenders, acting as stops for compression of the bottom transverse elements in register with the bottom side rails, or indeed for compression of the bottom portions of the uprights. Thus, the absorber frame bears not only at a high level in the vehicle, constituted in particular by the main side rails, but also at a low level of the vehicle.

Each top and bottom transverse element and each upright comprises absorber means for absorbing insurance type impacts. Thus, each of these means is capable of deforming as a result of such an impact, in order to prevent plastic deformation of the vehicle chassis (comprising in particular the top side rails and possibly also bottom side rails, etc.), or indeed plastic deformation of the radiator or of other elements fitted around the radiator. The term "plastic deformation" is used to mean irreversible deformation as a result of an impact. It should be observed that the means for absorbing insurance type impacts differ from the means for absorbing parking type impacts which are capable of absorbing relatively little energy by deforming, or indeed means for protecting pedestrians, and designed to handle impacts of the "leg impact" or "hip impact" or indeed "head impact" type. The person skilled in the art knows how to distinguish such insurance type impact absorber means. In any event, it can be considered that the module comprising the absorber frame and the central reinforcement is capable, by deforming, of providing at least 30% of the energy absorption in the event of an insurance type impact.

Above the top transverse element, the absorber module includes central reinforcement. By means of this reinforcement, which may also be referred to as a "plastron", it is possible to support the top portion of the bumper skin in the zone situated above the side rails, while reinforcing said skin, in particular providing an anti-denting function, and also a function of managing clearances and flush surfaces. This reinforcement may also perform a function of handling a pedestrian impact such as the "hip impact". The central reinforcement is a support for the vehicle bumper skin.

The central reinforcement includes the air-guide forming wall extending from the top transverse element towards the radiator. This provides a simple way of obtaining a module that performs impact absorption, streamlining, and bodywork support functions.

The module includes movable shutter means for shutting an air inlet, preferably provided in the bumper skin. In an embodiment, these movable means are designed to shut the above-described guide compartment defined by the absorber module. These shutter means preferably comprise pivoting louvers, capable of taking up a totally closed position in which the louvers are oriented so that together they define a solid surface that prevents air from passing through, and one or more open positions, in which the louvers define a surface that is perforated to a greater or lesser extent for allowing air to pass. The louvers are generally controlled automatically as a function of the speed of the vehicle, e.g. by motor-driven means or by an electromagnet. By way of example, provision can be made for the shutter means to take up a totally shut position when the vehicle is not moving or is operating at low power, and an open or semi-open position above a certain power level.

The invention also provides an assembly comprising an impact beam, a bottom structural part, and a module as defined above.

DESCRIPTION OF THE FIGURES

The invention can be better understood on reading the following description given purely by way of example and made with reference to the drawings, in which.

Figure 1:
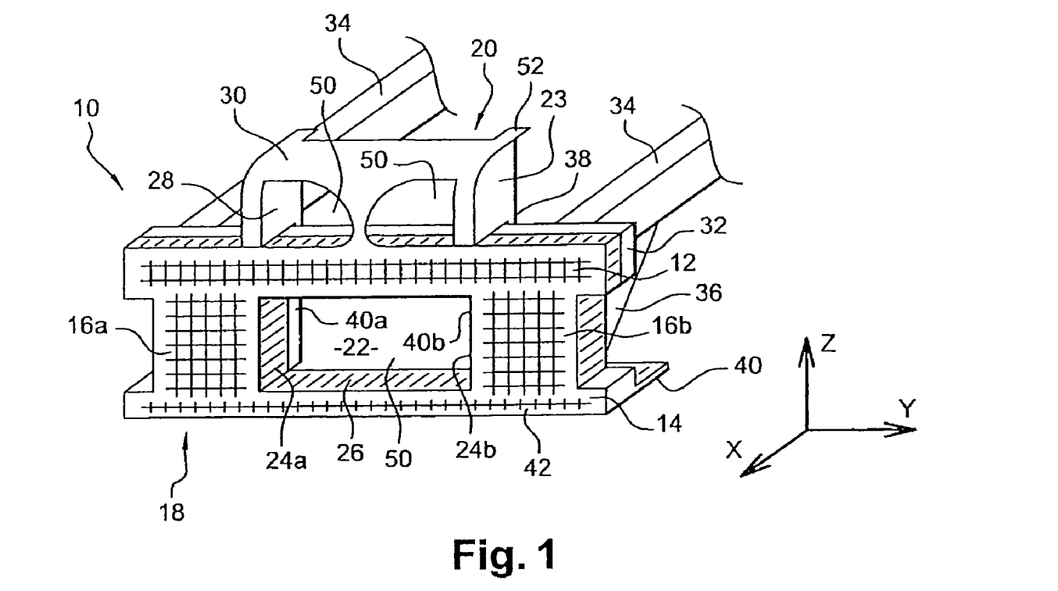
FIG. 1 is a perspective diagram of front portions of a vehicle including a module constituting a first embodiment of the invention.

As can be seen in the diagram of FIG. 1, an impact absorber module 10 includes a top transverse element 12, a bottom transverse element 14, and two uprights 16a and 16b interconnecting the top and bottom transverse elements 12 and 14 so as to form an absorber frame 18. The module 10 is made of plastics material, preferably of polypropylene. Each of the elements 12, 14, 16a, and 16b of the absorber frame 18 includes absorber means for absorbing impacts of the insurance type. In order to optimize absorption, these means ribs arranged as a honeycomb.

Figure 4:
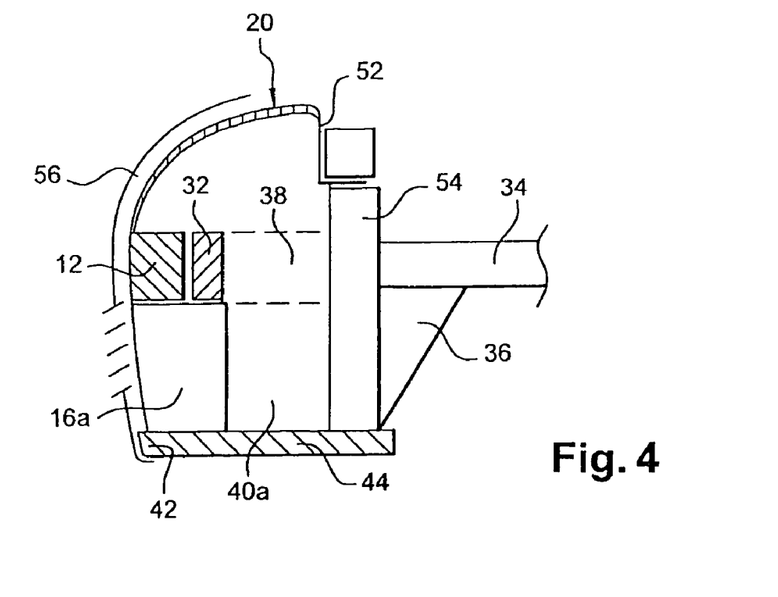
FIG. 4 is a diagrammatic section of a module that differs slightly from that of FIG. 1, shown mounted on the vehicle.

The module 10 also includes central reinforcement 20, also referred to as a "plastron", extending above the top element 12, and having a concave shape that is capable of substantially matching the inside shape of the bumper skin 56 of the vehicle, as can be seen in FIG. 4, thereby reinforcing it, in particular by supporting it and preventing the skin from blistering. It should be observed that this reinforcement 20 may also serve as a support for a bodywork part other than a bumper skin, and that it is capable of contributing to managing clearances and flush surfaces between different bodywork parts, e.g. the top of the bumper skin and the hood. This reinforcement 20 is also made of plastics material, being molded integrally with the absorber frame 18.

The module 10 defines a compartment 22 for guiding air towards the vehicle's radiator. The compartment 22 is defined in particular by the inside wall 24a or 24b of each of the uprights 16a and 16b, by the top wall 26 of the bottom transverse element 14, and by the inside walls of the central reinforcement 20, including vertical walls 28 and a substantially horizontal wall 30. The wall 30 serves in particular to form an air guide that extends from the top transverse element towards the radiator of the vehicle. Each of the walls 28 and 30 extends as far as the radiator when the module is mounted on the vehicle, possibly with the help of an extender wall.

An impact beam 32 is fitted to the module 10 so as to act as a bearing member for compressing the top transverse element 12. This impact beam 32 optionally includes on its rear face two absorbers or "crash-boxes" that are separate fittings or that are formed integrally therewith and that are located in register with the side rails 34 of the vehicle.

The module 10 and the impact beam 32 are fitted to the front chassis of the vehicle. In addition to two top side rails 34, the chassis includes two bottom structural parts 36 each extending downwards in line with the end of a respective one of the side rails 34 and presenting a bearing face so as to act as bearing surfaces for the uprights 16a and 16b, and possibly also for portions of the bottom transverse element 14 situated below the side rails. Each of these bottom structural parts 36 comprises a triangular brace capable of transferring to the bottom faces of the side rails 34 compression forces to which the uprights 16a, 16b are subjected, or resulting from the bottom element 14 being compressed against the bearing face of each part 36. These structural parts 36 are strong enough to remain intact on the vehicle in the event of an impact of the insurance type, i.e. they do not deform plastically.

Thus, in the event of an insurance impact, the elements 12, 14, 16a, and 16b of the module 10 are capable of deforming by being compressed against the side rails 34 and the bearing faces of the structural parts 36 so as to absorb the energy of the impact. This energy may also be absorbed by compressing the crash-boxes arranged on the impact beam 32. By virtue of impacts being absorbed in this way, the vehicle chassis is not deformed by an insurance type impact, and consequently the radiator that is arranged behind the module between the two side rails 34 is not damaged by the impact.

Figure 2:
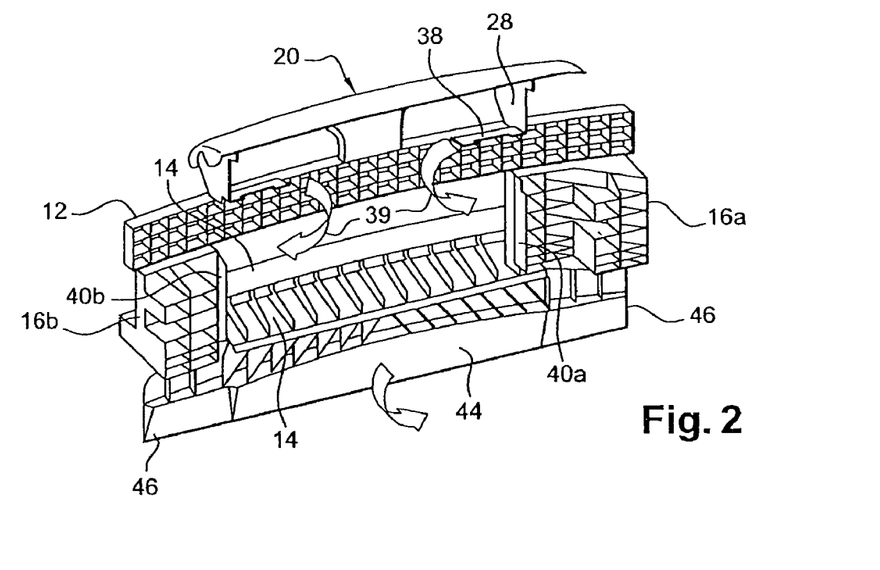
FIG. 2 is a rear view in perspective of an absorber module similar to that of FIG. 1, prior to being mounted on the vehicle.
Figure 3:
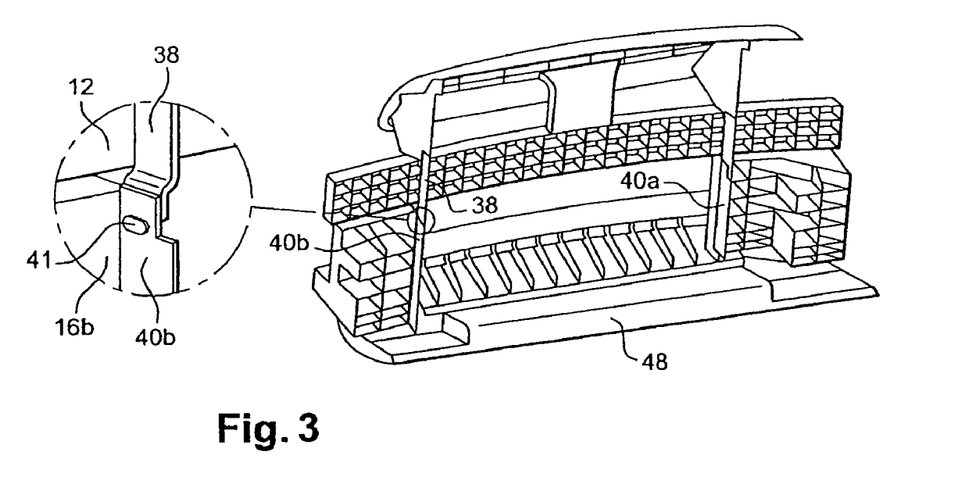
FIG. 3 is a view similar to FIG. 2 after the absorber module has been mounted on the vehicle.

In the configuration shown in FIG. 1, where the impact beam 32 carries crash-boxes (not shown), the guide compartment 22 is associated with tongues 38 integrally molded with the side walls 28 of the central upright 20 and capable of folding behind the impact beam 32 when it is fitted to the module 10, as represented by arrows 39 in FIG. 2. Such tongues 38 are connected to the side walls 28 by means of hinge films so as to be easily unmolded and folded to form an air guide between the impact beam 32 and the radiator, as can be seen in FIG. 3. They include fastener means 41 for fastening to bottom air guides 40a and 40b that extend the bottom walls 24a and 24b so as to fill the space formed between the uprights 16a and 16b and the radiator, thereby closing the guide compartment 22. The means for fastening the tongues 38 to the air guides 40a and 40b are preferably releasable, e.g. being in the form of clips.

Furthermore, the bottom transverse element 14 includes, on its face facing towards the bumper skin, a low bearing member 42 for handling a pedestrian impact known as a leg impact, together with a bottom spoiler 44 integrally molded therewith for guiding air towards the radiator. It should be observed that the low bearing member 42 bears against a pedestrian's leg in the event of an impact, for the purpose of sparing the knee. In order to stiffen this low bearing member 42, ribs are provided on the spoiler 44.

As can be seen in FIGS. 2 and 3, the spoiler 44 is molded on the module 10 so as to be retained by a hinge film. Thus, when the module 10 is fabricated, the spoiler extends vertically so as to enable the module 10 to be unmolded easily, as can be seen in FIG. 2. Thereafter, the spoiler 44 is molded so as to extend horizontally and perform its air-guiding function, as can be seen in FIG. 3.

In order to make the spoiler easier to fold, and also to avoid impeding compression of the uprights 16a and 16b, the spoiler 44 has two ends 46 that are not directly secured to the uprights 16a and 16b. In other words, the hinge film extends between the two uprights 16a and 16b but not under the uprights where it leaves the ends 46 free relative to the uprights. Thus, in the event of an impact, the uprights 16a and 16b together with the bottom transverse element 14 can deform and move back towards the side rails without the spoiler 44, which contributes a certain amount of stiffness in the longitudinal direction X, constituting an obstacle to such deformation.

Figure 5:
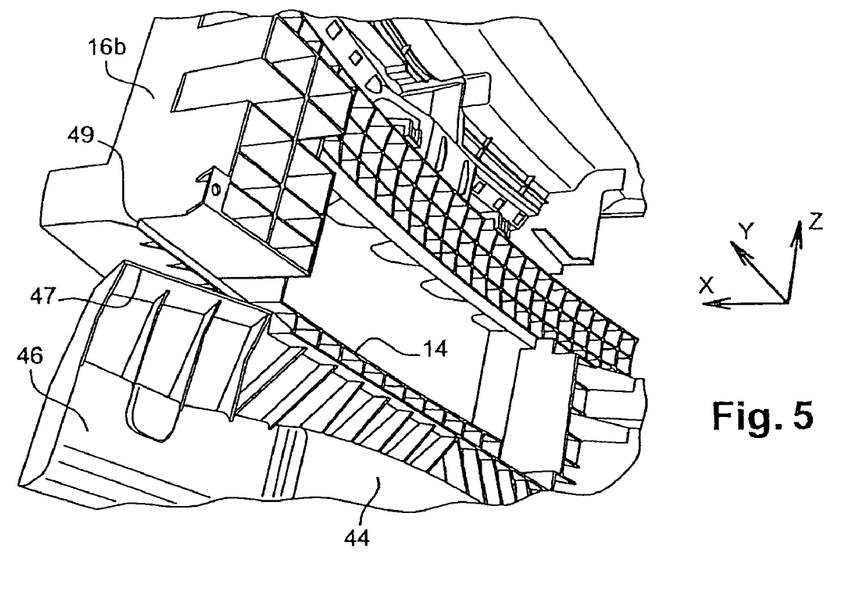
FIG. 5 is a fragmentary rear view of the FIG. 2 absorber module, seen from a different angle.
Figure 6:
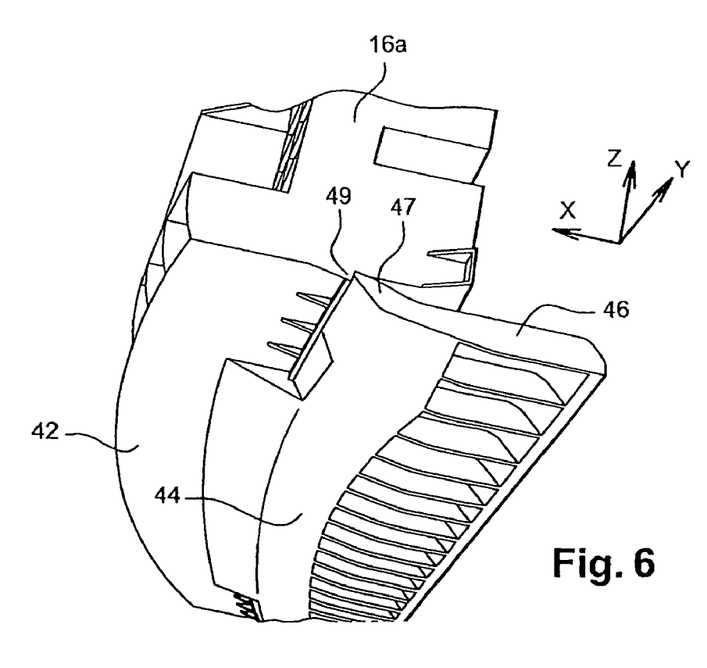
FIG. 6 is a fragmentary view from beneath of the FIG. 3 absorber module, seen from a different angle.

To enable the spoiler 44 to be held in its horizontal position, and to avoid vibration, wedging means 47 are provided in particular at the ends 46 for wedging the spoiler in the longitudinal direction X of the vehicle by co-operating with complementary wedging means 49 formed on the bottom walls of the uprights 16a and 16b, as can be seen in FIG. 5. These wedging means are capable of retracting in the event of an insurance type impact so that the uprights 16a and 16b can deform and move back in the direction X. These wedging means can be seen in FIG. 5 as means constituting abutments in the direction X, but provision could also be made for these means to form abutments in the vertical direction Z, thus providing the advantage of contributing to holding the spoiler 44 in its horizontal position. Such means forming vertical abutments could be in the form of a rib provided along and on the bottom of the abutment 49 so as to constitute breakable means for holding the spoiler 44 in its horizontal position, suitable for being forced in the event of an insurance impact so as to release the bottoms of the uprights 16a and 16b and prevent the spoiler 44 constituting an obstacle to them being compressed against the bottom structural parts 36 or against the bottom side rails.

The spoiler 44 also has stiffening ribs for the purpose of handling a leg impact effectively. It also has a cross-member 48, as can be seen in FIG. 3 that may either be fitted or molded integrally therewith, suitable for performing a function of stiffening the absorber frame, or the front of the vehicle in general, and in particular being suitable for carrying the radiator. By way of example, this cross-member may be fastened to the radiator.

It should be observed that the middle portion of the spoiler 44 situated between the two side rails may also include means for holding the spoiler 44 in its horizontal position and suitable for holding the spoiler in position in the event of a pedestrian impact, and of retracting to allow it to move backwards in the event of an insurance impact so as to facilitate absorption by deformation of the absorber frame 18.

Figure 7:
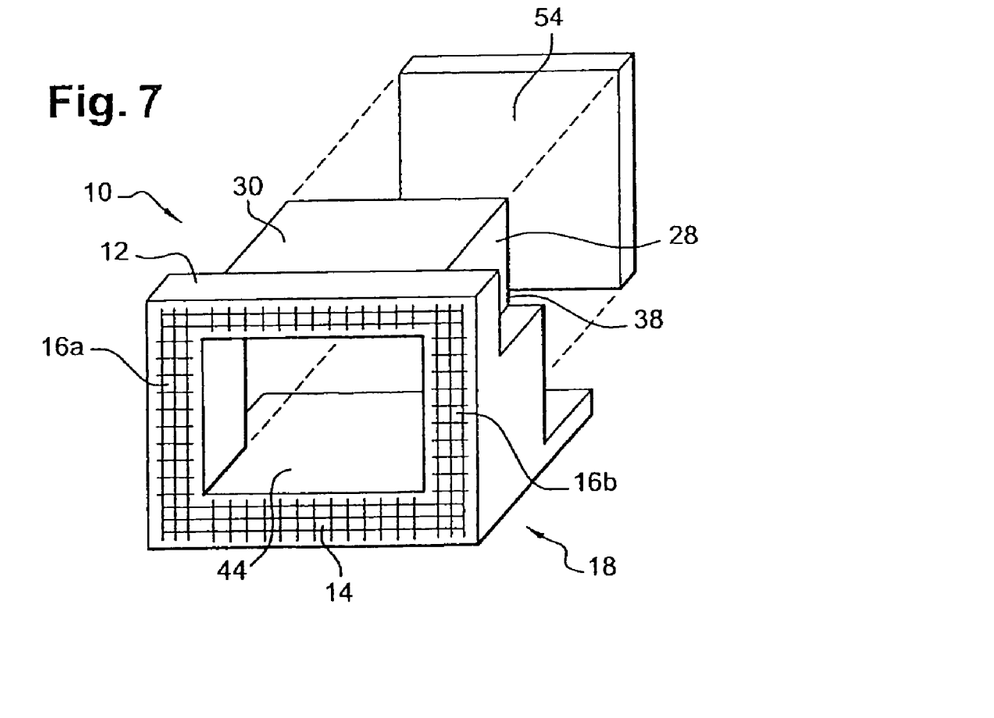
FIG. 7 is a perspective diagram of front portions of a vehicle including a module constituting a second embodiment of the invention.
Figures 8, 9:
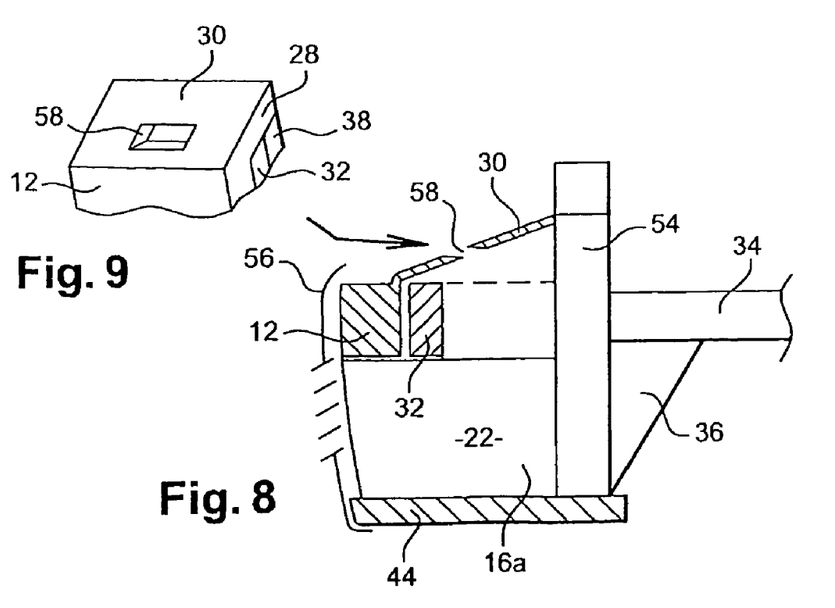
FIG. 8 is a diagrammatic section of a module that is slightly different from that of FIG. 7.
FIG. 9 is a face view of a portion of the FIG. 8 module.

In the embodiment of FIGS. 7 to 9, analogous elements are designated by identical references.

The wall 30 forming an air guide that extends from the two transverse elements 12 towards the radiator 54 is not an element of central reinforcement and in this example it has the function, in association with the walls 28 and the tongues 38, of shutting the top portion of the guide compartment 22. This wall 30 is in the form of a web that is substantially horizontal, but it could be inclined. In its center it preferably includes an opening 58 for passing air from top air inlets in the bumper skin into the guide compartment 22.

In order to provide good leaktightness for the air entering via the air inlets in the bumper skin, a duct may be provided that runs, for example, from a top air inlet in the skin to the opening 58 in the wall 30 so as to bring the air to the leaktight compartment 22.

It will be understood that by virtue of the various guide means 24a, 40a, 24b, 40b, 26, 28, 30, and 38, the compartment 22 constitutes a compartment that is particularly effective in guiding the air entering via openings formed in the bumper skin, entering via the openings 50 or 58 in the reinforcement 20 or the wall 30, or indeed via the center opening of the frame 18, and going towards the vehicle radiator 54, as represented diagrammatically in FIGS. 4 and 8. By making the various junctions between the air guides leaktight, it is possible to obtain a compartment that is capable of guiding air in leaktight manner, thereby providing a leaktight compartment that is particularly advantageous since, by virtue of its effectiveness in guiding air, it makes it possible to use radiators that are lower, thereby making it possible to reduce the overhang of the vehicle. This leaktightness is easier to achieve when these elements are molded together as a single piece.

Figure 10:
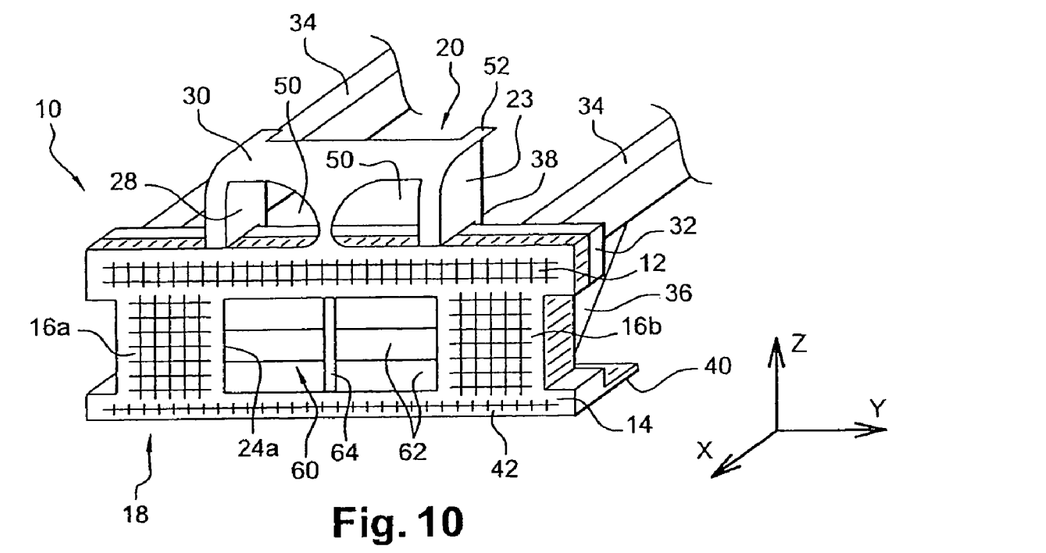
FIG. 10 is a view similar to that of FIG. 1, the absorber module including movable shutter means for shutting an air inlet, in the totally shut position.
Figure 11:
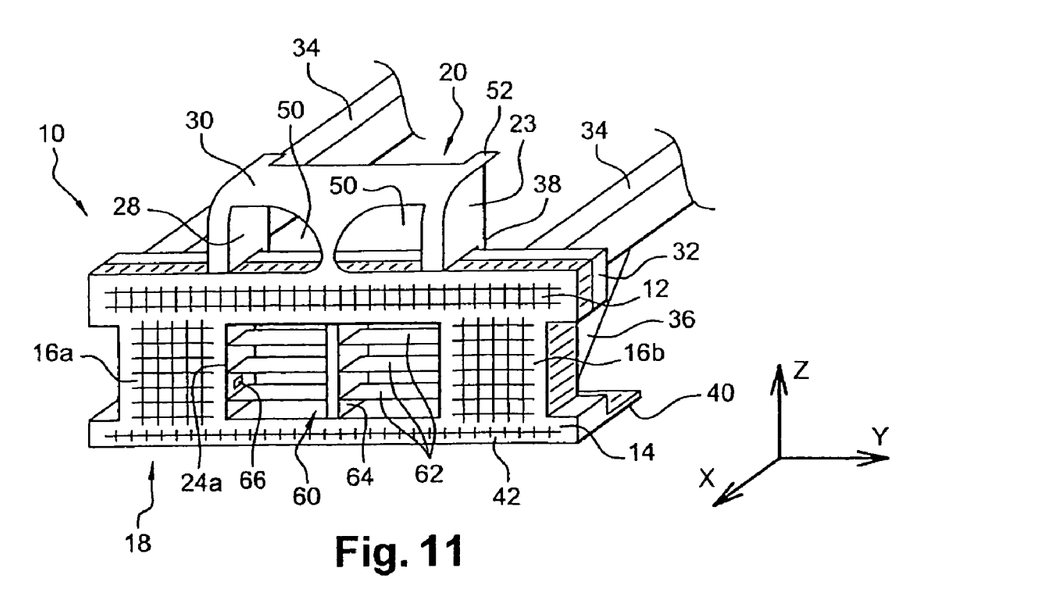
FIG. 11 is a view similar to FIG. 10, the movable shutter means being in the open position.

In an embodiment shown in FIGS. 10 and 11, the module 10 includes movable shutter means 60 for shutting an air inlet formed in the bumper skin, the means 60 being suitable for shutting the guide compartment 22. These means 60 comprise louvers 62 each pivotally mounted about a central longitudinal axis of the louver. In FIGS. 10 and 11, each louver axis 62 is mounted firstly on one or the other of the inside walls 24a and 24b and secondly on a vertical wall 64 interconnecting the front central portions of the elements 12 and 14.

The louvers 62 can take up a totally shut position as shown in FIG. 10, in which together they define a solid surface, and also one or more open positions, one of which is shown in FIG. 11. The louvers 62 are controlled by louver control means 66, e.g. motor-driven means or an electromagnet. These means 66 are operated automatically as a function of the speed of the vehicle. In this example, the means 66 are mounted on one or other of the uprights 16a or 16b, e.g. on the inside wall 24a or 24b, and they are preferably not visible from outside the vehicle.

It will be understood that means similar to the means 60 can be used in other embodiments of the absorber module, and can shut any type of air inlet.

It should be observed that the module 10, in association with the impact beam 32, can be assembled away from the vehicle assembly line so as to be fitted to the chassis as a single unit, possibly incorporating the shutter means 60. It may be fastened at various points provided on the elements 12, 14, 16a, and 16b, and also using means 52 provided on the central reinforcement 20 or the wall 30 enabling the reinforcement or the wall 30 to be fastened to the radiator or to a cross-member supporting the radiator.

It should also be observed that the module 10 may also include incorporate numerous other functions, such as the function of supporting fasteners, bundles, sensors, a horn, guiding air towards some element other than the radiator, e.g. a supercharger air radiator that may be provided above the main radiator, or to one side, at the outside end of one of the uprights 16a, 16b.

Finally, it should be observed that the invention is not limited to the above-described embodiments.

In particular, in an embodiment that is not described, the rear chassis of the vehicle does not include the structural parts 36 that could be called brackets, but rather bottom side rails, or indeed it could include both such hangers 36 and bottom side rails, thereby enabling the force received by the bottom ends of the brackets to be taken up.

The invention claimed is:

1. An impact absorber module for a motor vehicle, the module comprising:
   a top transverse element for bearing against an impact beam of the vehicle;
   a bottom transverse element and two uprights connecting the top and bottom transverse elements together so as to form an absorber frame, each top and bottom transverse element and each of the two uprights comprising absorber means for absorbing insurance type impacts; at least one of the bottom transverse element and the two uprights being designed to bear against a bottom structural part of the vehicle, the bottom structural part being configured so that it does not deform irreversibly in the event of an insurance type impact; and a wall forming an air guide and extending from the top transverse element towards a radiator of the vehicle.

2. An absorber module according to claim 1, wherein the absorber frame and the wall forming the air guide are made of plastics material.

3. An absorber module according to claim 1, the absorber module defining a compartment for guiding air towards the radiator, the compartment being defined by an inside wall of each of the uprights, a top wall of the bottom transverse element, and the wall forming the air guide extending from the top transverse element.

4. An absorber module according to claim 3, including air-guide means arranged between the impact beam and the radiator.

5. An absorber module according to claim 3, the absorber module defining a leaktight compartment suitable for guiding incoming air towards the radiator in a leaktight manner.

6. An absorber module according to claim 1, wherein the bottom transverse element includes a bottom spoiler.

7. An absorber module according to claim 1, wherein the bottom structural part is suitable for remaining intact after an insurance type impact.

8. An absorber module according to claim 1, wherein the two uprights are designed to bear against a structural part including a bearing face and extending downwards in line with an end of each side rail.

9. An absorber module according to claim 8, wherein the structural part comprises a brace.

10. An absorber module according to claim 1, wherein the bottom structural part comprises bottom side rails.

11. An absorber module according to claim 1, including central reinforcement above the top transverse element.

12. An absorber module according to claim 11, wherein the central reinforcement includes the wall forming the air guide extending from the top transverse element towards the radiator.

13. An absorber module according to claim 1, including movable shutter means for shutting an air inlet.

14. An assembly comprising an impact beam, a bottom structural part and a module according to claim 1.

15. An absorber module according to claim 3, wherein each of the inside walls, the top wall and the wall forming the air guide extend as far as the radiator.

16. An absorber module according to claim 4, wherein the air-guide means is integrally molded with the wall forming the air guide extending from the top transverse element.

17. An absorber module according to claim 11, wherein the central reinforcement is a support for a vehicle bumper skin.

* * * * *